ns(12) United States Patent
Giles et al.

US008801962B2

(10) Patent No.: US 8,801,962 B2
(45) Date of Patent: Aug. 12, 2014

(54) CHELATING AGENTS AND METHODS RELATING THERETO

(75) Inventors: Matthew Robert Giles, Chester (GB); Nicholas John Dixon, Chester (GB)

(73) Assignee: Innospec Limited (GB)

( * ) Notice: Subject to any disclaimer, the term of this patent is extended or adjusted under 35 U.S.C. 154(b) by 403 days.

(21) Appl. No.: 13/146,322

(22) PCT Filed: Jan. 21, 2010

(86) PCT No.: PCT/GB2010/050088
§ 371 (c)(1),
(2), (4) Date: Aug. 23, 2011

(87) PCT Pub. No.: WO2010/084351
PCT Pub. Date: Jul. 29, 2010

(65) Prior Publication Data
US 2012/0068113 A1    Mar. 22, 2012

(30) Foreign Application Priority Data

Jan. 26, 2009  (GB) .................................. 0901207.1

(51) Int. Cl.
*D06L 3/02* (2006.01)
*C01B 15/01* (2006.01)
*C01B 15/03* (2006.01)
*C01B 15/12* (2006.01)
*C11D 3/39* (2006.01)
*C07C 229/00* (2006.01)
*C07C 229/24* (2006.01)

(52) U.S. Cl.
USPC ............ 252/186.29; 252/186.27; 252/186.28; 252/186.31; 252/186.26; 252/186.25; 562/568; 562/571

(58) Field of Classification Search
CPC .............................. C01B 15/037; D06L 3/021
USPC .................................................. 252/186.29
See application file for complete search history.

(56) References Cited

U.S. PATENT DOCUMENTS

| 3,211,658 | A | | 10/1965 | Hirtz et al. |
| 4,155,738 | A | | 5/1979 | Boghosian |
| 4,195,974 | A | * | 4/1980 | Kothe et al. ........................ 8/138 |
| 4,392,975 | A | * | 7/1983 | Tourdot et al. ..................... 8/111 |
| 4,430,243 | A | * | 2/1984 | Bragg ............................ 510/311 |
| 4,596,765 | A | | 6/1986 | Kurematsu et al. |
| 4,695,397 | A | * | 9/1987 | Sommer et al. .................. 524/41 |
| 5,055,286 | A | * | 10/1991 | Watanabe et al. ............. 423/584 |
| 5,332,518 | A | * | 7/1994 | Kuroda et al. .................. 510/309 |
| 5,786,313 | A | | 7/1998 | Schneider |
| 5,885,412 | A | * | 3/1999 | Paart et al. ........................ 162/5 |
| 5,922,307 | A | * | 7/1999 | Montgomery .................. 424/53 |
| 6,160,194 | A | * | 12/2000 | Pignatello .................. 405/128.5 |
| 6,218,352 | B1 | | 4/2001 | Lee et al. |
| 6,488,914 | B2 | * | 12/2002 | Montgomery .................. 424/53 |
| 8,377,478 | B2 | * | 2/2013 | Giles et al. .................... 424/489 |
| 2002/0141951 | A1 | * | 10/2002 | Montgomery .................. 424/53 |
| 2005/0255172 | A1 | * | 11/2005 | Omidbakhsh ................. 424/616 |
| 2006/0100122 | A1 | * | 5/2006 | Baars et al. .................... 510/375 |
| 2007/0166398 | A1 | * | 7/2007 | Bobbert ........................ 424/616 |
| 2007/0190172 | A1 | * | 8/2007 | Bobbert ........................ 424/616 |
| 2007/0231276 | A1 | * | 10/2007 | Sharma et al. ................... 424/53 |
| 2007/0231277 | A1 | * | 10/2007 | Sharma et al. ................... 424/53 |
| 2008/0305182 | A1 | * | 12/2008 | Ramirez et al. ............... 424/616 |
| 2010/0236734 | A1 | * | 9/2010 | Giles et al. ....................... 162/76 |
| 2013/0206181 | A1 | * | 8/2013 | Giles et al. ................... 134/25.2 |

FOREIGN PATENT DOCUMENTS

| EP | 0186990 | A2 | 7/1985 |
| EP | 0317542 | A2 | 5/1989 |
| EP | 0399133 | A1 | 11/1990 |
| EP | 0476257 | A1 | 3/1992 |
| EP | 0509382 | A2 | 10/1992 |
| EP | 0516102 | A1 | 12/1992 |
| EP | 0570331 | A1 | 11/1993 |
| EP | 1 359 140 | A1 | 11/2003 |
| GB | 2 347 671 | B | 9/2000 |
| JP | 2004-035549 | A | 2/2004 |
| WO | 9116073 | A1 | 10/1991 |
| WO | 97/30208 | | 8/1997 |
| WO | 97/30209 | | 8/1997 |
| WO | 99/46441 | | 9/1999 |
| WO | 2007085579 | A1 | 8/2007 |

OTHER PUBLICATIONS

International Search Report from International Parent Application No. PCT/GB2010/050088, Priority Date, Jan. 26, 2009, mailed Apr. 20, 2010.
Database: Beilstein (Apr. 2009), XP-002571085, Feb. 25, 2010, CrossFire Beilstein Database, Copyright © 2007-2009, Elsevier Properties S.A., Licensed to Elsevier Information Systems GmbH.
Database: Beilstein (Apr. 2009), XP-002571086, Feb. 25, 2010, Cross Fire Beilstein Database, Copyright © 2007-2009, Elsevier Properties S.A., Licensed to Elsevier Information Systems GmbH.
Database: Beilstein (Apr. 2009), XP-002571087, Feb. 25, 2010, Cross Fire Beilstein Database, Copyright © 2007-2009, Elsevier Properties S.A., Licensed to Elsevier Information Systems GmbH.
Database: Beilstein (Apr. 2009), XP-002571088, Feb. 25, 2010, CrossFire Beilstein Database, (4 Pages), Copyright © 2007-2009, Elsevier Properties S.A., Licensed to Elsevier Information Systems GmbH.
G.H. Nancollas et al., "Proton Magnetic Resonance Studies on some Metal Complexes of Methyliminodiacetic Acid and Hydroxyethyliminodiacetic Acid," Chemistry Department, State University of New York at Buffalo, Buffalo, New York 14814 (Received May 25, 1967) The Journal of Physical Chemistry, XP-002571089, vol. 71, No. 11, Oct. 1967, pp. 3678-3681.
International Preliminary Report on Patentability and the Written Opinion of the International Searching Authority from corresponding parent international patent application PCT/GB2010/050088, filed Jan. 21, 2010 with an earlier priority date of Jan. 26, 2009.

* cited by examiner

*Primary Examiner* — Joseph D Anthony
(74) *Attorney, Agent, or Firm* — Burns & Levinson LLP; Janine M. Susan

(57) ABSTRACT

A salt of an acidic chelating agent including an amine functionality, the salt comprising at least 0.25 mole of an alkaline earth metal per mole of acidic protons provided by the chelating agent; wherein the acidic chelating agent is not ethylene diamine disuccinic acid.

10 Claims, No Drawings

CHELATING AGENTS AND METHODS RELATING THERETO

CROSS-REFERENCE TO RELATED APPLICATIONS

This application is a U.S. national stage application under 35 U.S.C. 371 of co-pending International Application No. PCT/GB10/050088 filed Jan. 21, 2010, which in turn claims priority to Great Britain Patent Application No. 0901207.1 filed Jan. 26, 2009 each of which is incorporated by reference herein in its entirety for all purposes.

The present invention relates to alkaline earth metal salts of chelating agents, to compositions comprising the same, and to methods and uses relating thereto. The invention relates in particular to such salts, compositions, methods and uses giving good oxidation stability.

The present invention relates especially to chelating agents of heavy metals and transition metals, in particular for use in bleaching applications.

Active oxygen based bleaching compositions including compounds such as peroxides and peracids are commonly used in a wide variety of applications, for example in laundry, dishwashing and other cleaning compositions; in pulp and paper bleaching; and in personal care compositions.

It is known that heavy metals and transition metals, for example manganese, iron and copper degrade peroxygen species. It is therefore common to include chelating agents to bind to these metals in compositions containing peroxide and the like.

Many common transition metal chelating agents include an amine functional group. However in the presence of a peroxygen species, the amine moiety may be oxidized. Thus the chelating agent itself may also contribute to degradation of the peroxide or peracid present in a bleaching composition.

Thus there exists a need to provide improved chelating agents which are more effective at improving the stability of peroxygen bleaching agents.

Such improvements may be beneficial in terms of cost effectiveness and overall performance or may allow lower treat rates to be used to provide equivalent performance.

It is an aim of the present invention to provide a source of chelating agent which when included in a composition comprising peroxide leads to improved peroxide stability.

According to a first aspect of the present invention there is provided a salt of an acidic chelating agent including an amine functionality, the salt comprising at least 0.25 mole of an alkaline earth metal per mole of acidic protons provided by the chelating agent; wherein the acidic chelating agent is not ethylene diamine disuccinic acid.

The definition of the first aspect of the present invention refers to the number of moles of acidic protons provided by the chelating agent. For the avoidance of doubt, this refers to the total number of acidic protons provided by the free acid before any neutralisation/salt formation has occurred. In the salt itself some or all of the acidic protons will have been neutralised.

It will be appreciated that an acidic chelating agent may include one or more acidic groups. Each acidic group may be monobasic or dibasic. It will be understood that the number of protons provided by a particular acidic group depends on whether the acidic group is a monobasic acidic group or dibasic acidic group. A monobasic acidic group is one which contains only one replaceable hydrogen atom, for example a carboxylic acid, RCOOH. A dibasic acidic group is one which contains two replaceable hydrogen atoms, for example a phosphonic acid RP=O(OH)$_2$.

The number of moles of protons provided per mole of acidic chelating agent depends on the number of acidic groups present in the chelating group and whether each acidic group is monobasic or dibasic. For one mole of chelating agent, each monobasic acid group present will contribute a mole of acidic protons. Thus one mole of a chelating agent having two monobasic acidic groups will provide 2 moles of acidic protons; one mole of a chelating agent having three monobasic acidic groups will provide 3 moles of acidic protons; and so on. Likewise, one mole of chelating agent including one dibasic acidic group will provide 2 moles of acidic protons and one mole of a chelating group having two dibasic acidic groups will provide 4 moles of acidic protons.

Preferably the salt comprises at least 0.3 mole of alkaline earth metal per mole of acidic protons provided by the chelating agent, more preferably at least 0.35 mole, for example at least 0.4 mole, preferably at least 0.45 mole, more preferably at least 0.48 mole, and most preferably approximately 0.5 moles.

Because alkaline earth metal cations have a charge of +2, each mole of alkaline earth metal cations can replace two moles of acidic protons in a neutralisation reaction.

Thus a salt in which approximately 0.5 moles of alkaline earth metal per mole of acidic protons is present is one in which substantially all of the acidic protons have been neutralised.

The present invention provides the salt of an acidic chelating agent including an amine functionality in which at least 50% of the acidic protons have been replaced by an alkaline earth metal counter ion, preferably at least 60%, more preferably at least 70%, for example at least 80%, preferably at least 90%, more preferably at least 95% and most preferably at least 98% have been replaced by an alkaline earth metal counter ion.

Preferably the alkaline earth metal is selected from calcium, magnesium, and mixtures thereof.

The presence of cations other than of alkaline earth metals in salt of the first aspect is not excluded, provided that the salt includes at least 0.25 mole of alkaline earth metal ions per mole of acidic protons. Such further cations may include alkali metal ions, for example sodium or potassium.

However in preferred embodiments, the salt of the present invention does not comprise an alkali metal. In especially preferred embodiments the salt comprises only an alkaline earth metal and an acidic chelating agent.

The acidic chelating agents of the present invention include an amine functionality. Acidic chelating agents including an amine functionality will be well known to the person skilled in the art.

Preferred chelating agents of the present invention are aminocarboxylic acid chelating agents and amino phosphonic acid chelating agents. The active species provided by such chelating agents are typically present in solution as the anionic aminocarboxylates or aminophosphonates. Especially preferred chelating agents are those derived from aminopolycarboxylic acids and amino polyphosphonic acids. Most preferably the chelating agent is derived from an aminopolycarboxylic acid.

Suitable amino phosphonic acid-containing chelating agents having an amino functionality include organic amino phosphonic acids, such as the amino alkylene poly(alkylene phosphonic) acids. Preferred chelating agents of this type include ethylene diaminetetramethylene phosphonic acid and preferably diethylene triamine penta (methylene phosphonic acid), ethylene diamine tri (methylene phosphonic acid) and hexamethylene diaminetetra(methylene phosphonic acid).

Such phosphonic acid chelating agents are commercially available from ThermPhos under the tradename Dequest®, typically as a sodium salt thereof. A suitable chelating agent can be amino tri (methylene phosphonic acid).

Suitable amino carboxylic acid-containing chelating agents having an amino functionality for use in the present invention include polyaminocarboxylic acids for example ethylenediaminotetraacetic acid (EDTA), ethyenetriamine pentaacectic acid, ethylenediaminediglutaric acid, 2-hydroxypropylenediamine disuccinic acid, diethylene triamine pentaacetic acid (DTPA), N-hydroxyethylethylenediamine triacetic acid, ethylenediamine tetrapropionic acid, triethylenetetraaminehexa-acetic acid, ethanol-diglycines, propylene diamine tetracectic acid (PDTA) and methyl glycine diacectic acid (MGDA). Suitable amino carboxylic acids to be used herein are diethylene triamine penta acetic acid, propylene diamine tetracetic acid (PDTA) which is, for instance, commercially available from BASF under the tradename Trilon FS® and methyl glycine di-acetic acid (MGDA).

Other suitable chelating agents for use herein are iminodiacetic acid derivatives such as 2-hydroxyethyl diacetic acid or glyceryl immino diacetic acid, described in EP-A-317,542 and EP-A-399,133. The iminodiacetic acid N-2-hydroxypropyl sulfonic acid and aspartic acid N-carboxymethyl N-2-hydroxypropyl-3-sulfonic acid chelating agents described in EP-A-516,102 are also suitable herein. The β-alanine-N,N'-diacetic acid, aspartic acid-N,N'-diacetic acid, aspartic acid-N-monoacetic acid and iminodisuccinic acid sequestrants described in EP-A-509,382 are also suitable.

EP-A-476,257 describes suitable amino based chelating agents. EP-A-510,331 describes suitable chelating agents derived from collagen, keratin or casein. EP-A-528,859 describes a suitable alkyl iminodiacetic acid chelating agent. Glycinamide-N,N' disuccinic acid (GADS), ethylenediamine-N,N'-diglutaric acid (EDDG) and 2-hydroxypropylenediamine-N-N'-disuccinic acid (HPDDS) are also suitable.

Preferably the chelating agent is selected from methylglycinediacetic acid (MGDA), glutamic acid, N,N-diacetic acid (GLDA), iminodisuccinic acid (IDS); ethylenediaminetetraacetic acid (EDTA) diethylenetriaminepentaacetic acid (DTPA), diethylenetriamine-penta-methylene phosphonic acid (DETPMP), hydroxyethyliminodiacetic acid (HEIDA), Nitrilotriacetic acid (NTA), aspartic acid diethoxysuccinic acid (AES), aspartic acid-N,N-diacetic acid (ASDA), diethylenetriaminepentamethylene-phosphonic acid (DTPMPA), hydroxyethylenediaminetetraacetic acid (HEDTA), hydroxyethylethylenediaminetriacetic acid (HEEDTA), iminodifumaric (IDF), iminoditartaric acid (IDT), iminodimaleic acid (IDMAL), iminodimalic acid (IDM), ethylenediaminedifumaric acid (EDDF), ethylenediaminedimalic acid (EDDM), ethylenediaminediditartaric acid (EDDT), ethylenediaminedimaleic acid and (EDDMAL), aminotri(methylene-phosphonic acid) (ATMP).

More preferably the chelating agent is selected from iminodisuccinic acid (IDS), ethylenediaminetetraacetic acid (EDTA) diethylenetriaminepentaacetic acid (DTPA), hydroxyethylenediaminetetraacetic acid (HEDTA), hydroxyethylethylenediaminetriacetic acid (HEEDTA), iminodifumaric (IDF), iminoditartaric acid (IDT), iminodimaleic acid (IDMAL), iminodimalic acid (IDM), ethylenediaminedifumaric acid (EDDF), ethylenediaminedimalic acid (EDDM), ethylenediaminediditartaric acid (EDDT), ethylenediaminedimaleic acid (EDDMAL) and aminotri(methylene-phosphonic acid) (ATMP).

Suitably the acidic chelating agent is selected from MGDA, GLDA, IDS, EDTA, DTPA, DETPMP, HEIDA, NTA, AES, ASDA, DTPMPA AND HEDTA.

Preferably the acidic chelating agent is selected from MGDA, GLDA, IDS, EDTA, DTPA, DETPMP and HEIDA.

Methylglycinediacetic acid (MGDA) has the structure shown in formula I:

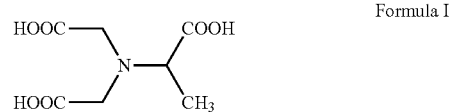

Formula I

MGDA may be present as either enantiomer or a mixture thereof. Preferably it is present as a racemic mixture.

Glutamic acid N,N-diacetic acid (GLDA) has the structure shown in formula II:

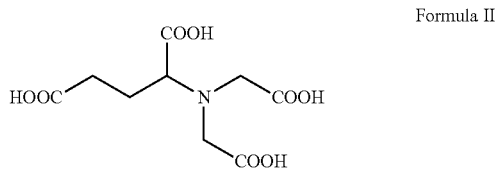 [SMILES: O=C(O)CCC(C(=O)O)N(CC(=O)O)CC(=O)O]

Formula II

GLDA may be present as either enantiomer or a mixture thereof. In some preferred embodiments the GLDA consists essentially of the S enantiomer.

DTPA has the structure shown in formula III:

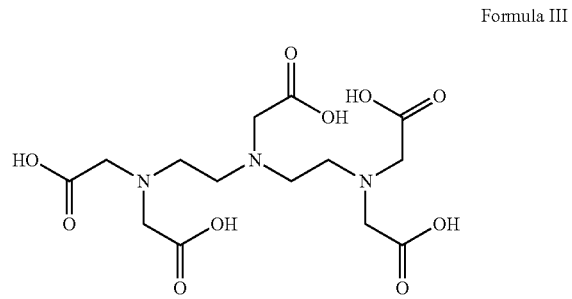 [SMILES: O=C(O)CN(CCN(CC(=O)O)CC(=O)O)CCN(CC(=O)O)CC(=O)O]

Formula III

EDTA has the structure shown in formula V:

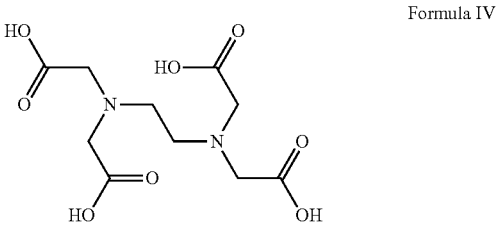 [SMILES: O=C(O)CN(CCN(CC(=O)O)CC(=O)O)CC(=O)O]

Formula IV

DETPMP has the structure shown in formula V:

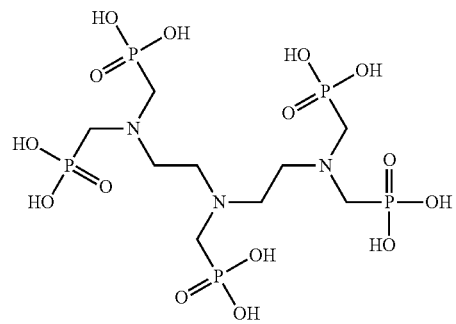

Formula V

Iminodisuccinic acid (IDS) has the structure shown in formula VI:

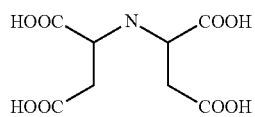

Formula VI

In this specification IDS is used to refer to the structure shown in formula VI and the same structure in which a number of the acidic protons have been replaced, i.e. in which 1, 2, 3 or 4 of the acid groups have been neutralised or partially neutralised.

When component (a) comprises IDS or a salt thereof this may be present as either enantiomer or a mixture thereof. Preferably it is present as a racemic mixture.

IDS is commercially available as a solution comprising 34 wt % of the tetrasodium salt and is sold under the trade mark Baypure CX100.

Hydroxyethyliminodiacetic acid (HEIDA) has the structure shown in formula VII:

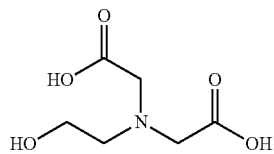

Formula VII

In this specification, the term HEIDA is used to refer to the structure shown in formula VII and the same structure in which a number of the acidic protons have been replaced, i.e. in which 1 or 2 of the acid groups have been neutralised or partially neutralised.

HEIDA is commercially available from Dow Chemicals.

In some preferred embodiments the present invention provides a salt comprising at least 1 mole of alkaline earth metal per mole of IDS, preferably at least 1.25 mole, more preferably at least 1.5 moles, for example at least 1.75 moles or at least 1.9 moles. In an especially preferred embodiment the salt comprises approximately 2 moles of alkaline earth metal per mole of IDS.

In some preferred embodiments the present invention provides an alkaline earth metal salt of HEIDA comprising at least 0.5 mole of alkaline earth metal per mole of HEIDA, preferably at least 0.7 mole, preferably at least 0.8 mole, more preferably at least 0.9 mole, for example at least 0.95 mole. In an especially preferred embodiment the salt comprises approximately 1 mole of alkaline earth metal per mole of HEIDA.

Examples of suitable salts of the present invention include dicalcium iminodisuccinic acid ($Ca_2IDS$), calcium magnesium iminodisuccinic acid (CaMgIDS), dimagnesium iminodisuccinic acid ($Mg_2IDS$), dicalcium hydroxyethyliminodiacetic acid ($Ca_2HEIDA$), calcium magnesium hydroxyethyliminodiacetic acid (CaMgHEIDA) and dimagnesium hydroxyethyliminodiacetic acid (MgHEIDA) and non-stoichiometric equivalents thereof.

Further suitable salts for use in the present invention include dicalcium, calcium magnesium and dimagnesium salts of GLDA, EDTA, DTPA, DETPMP and MGDA In some especially preferred embodiments, the acidic chelating agent is selected from IDS and HEIDA.

In embodiments in which the acid comprises one or more chiral centres the acid portion of the salt of the present invention may include any of the stereoisomers. The first aspect of the present invention also includes mixed salts compromising a mixture of more than one acid and/or a mixture of more than alkaline earth metal.

In some embodiments the salt of the first aspect of the present invention is a solid. It may be provided in the form of a free flowing particulate material. It may be a powder or it may be granular. Suitably the salt may be easily incorporated in a granular composition.

According to a second aspect of the present invention, there is provided a composition comprising a salt of the first aspect.

The composition may consist essentially of the salt of the first aspect or it may include one or more further components. Preferably the composition further comprises a source of peroxide. Sources of peroxide include hydrogen peroxide, other peroxygen-containing compounds and precursors thereof. For example the composition may comprise a perborate or a percarbonate compound.

A particular advantage of the composition of the present invention is that it improves the stability of hydrogen peroxide in an aqueous solution. In particular, the present invention provides the use of a salt of the first aspect to improve the stability of hydrogen peroxide or other peroxygen-containing compound or precursor thereof in alkaline solution. Compositions of the second aspect comprising a salt of the first aspect and a source of peroxide preferably have a pH of greater than 7.5, for example of between 8 and 14.

Thus the present invention further provides the use of a salt of the first aspect to improve the stability of a composition comprising hydrogen peroxide or other peroxygen-containing compound or precursor thereof.

One way of measuring the stability of a peroxide-containing composition is to measure how the concentration of peroxide falls over time. This can be carried out by titration with potassium permanganate at set intervals.

Preferably the salt of the present invention stabilises a composition comprising hydrogen peroxide to an extent that at least 65% of the initial hydrogen peroxide remains after a period of one hour, preferably at least 70%, more preferably at least 75%, for example at least 80%.

Suitably when a salt of the present invention is included in a composition comprising hydrogen peroxide, preferably at least 15% additional hydrogen peroxide remains after a period of one hour compared to an equivalent composition in which said salt is absent, more preferably at least 20% additional peroxide remains, preferably at least 25%, suitably at least 30%, for example at least 35% or at least 40% additional peroxide remains.

The inventors have also discovered that the stability of a salt of the first aspect in compositions which comprise hydrogen peroxide or other peroxygen containing compound or precursor thereof is greater than the stability of the corresponding free acid or sodium salts of the acid in a composition comprising hydrogen peroxide or other peroxygen containing compound or precursor thereof.

Thus the present invention further provides a composition comprising a salt of the first aspect and hydrogen peroxide or other peroxygen containing compound or precursor thereof said composition having increased stability compared with a solution having an equivalent amount of a sodium salt of the same acid and hydrogen peroxide or other peroxygen containing compound or precursor thereof. By an equivalent amount of a sodium salt of the same acid, we mean that the same molar ratio of acid anion is used.

Preferably when a salt of the present invention is used to replace an equivalent amount of a sodium salt of the same acid in a composition comprising hydrogen peroxide, at least 10% more hydrogen peroxide remains after a period of one hour, for example at least 15% more, preferably at least 20%.

The composition may be a solid composition or a liquid composition.

The composition may, for example, be a laundry composition or an automatic dishwashing composition. The composition may be in the form of a powder, for example a free flowing powder. Alternatively the composition may be in the form of compressed tablets, or encased, in liquid or solid form, in a shell of a water-soluble polymeric material. An alternative formulation vehicle, for example a gel or water-soluble capsule could also be used.

The composition may be a granular composition.

Solid laundry compositions of the present invention preferably comprise from 0.01 to 10 wt %, more preferably 0.01 to 2 wt %, most preferably 0.1 to 0.5 wt % of a salt of the first aspect.

Liquid laundry compositions of the present invention preferably comprise from 0.01 to 25 wt %, more preferably 0.1 to 10 wt %, most preferably 1 to 5 wt % of a salt of the first aspect.

Automatic dishwashing compositions of the present invention preferably comprise 0.1 to 60 wt % of a salt of the first aspect, more preferably 1 to 30 wt % and most preferably 2 to 15 wt %.

Laundry and dishwashing compositions of the present invention preferably comprise further ingredients selected from surfactants, builders, bleaches, bleach activators, redeposition additives, dye transfer inhibitors, enzymes, colorants and fragrances.

The composition of the present invention may be a bleaching composition. It may be a cleaning composition. It may be personal care composition. Personal care compositions include skin care compositions, for example cleansers, moisturisers and emollients; hair care compositions, for example shampoos, hair colouring compositions, hair lightening compositions and conditioning agents; and dental compositions, for example toothpaste, tooth whitening and mouthwash compositions.

In some preferred embodiments, the compositions of the present invention contain from 0.001 to 50 wt %, preferably 1 to 35 wt %, for example 5 to 10 wt % of hydrogen peroxide and from 0.001 to 10 wt %, preferably 0.01 to 1 wt % of the salt of the first aspect. Such compositions are suitably aqueous compositions.

These compositions are particularly useful in paper and pulp bleaching, and may also find utility in laundry and dishwashing applications.

According to a third aspect of the present invention there is provided a method of preparing a salt according to the first aspect.

Preferably the method of the third aspect involves mixing a base or a salt of an alkaline earth metal with an acidic chelating agent having an amine functionality wherein the acidic chelating agent is present as the free acid or an alkali metal salt thereof. In some preferred embodiments the method of the third aspect involves adding a base of an alkaline earth metal to a solution or suspension of the acidic chelating agent as the free acid, preferably an aqueous solution or suspension.

Any suitable base can be used. For example, the base may be selected from carbonates, bicarbonates, hydroxides, hydrides, amides and oxides. Preferably the base is magnesium hydroxide. The base may be added neat. Preferably however it is added in an aqueous solution.

In some preferred embodiments, the method of the third aspect may comprise adding an alkaline earth metal salt to a solution or suspension of an alkali metal salt of the acidic chelating agent.

It is believed that in such embodiments there is an ion exchange reaction in solution. Suitably the alkali metal counter ions of the acid are replaced with alkaline earth counter ions. In some preferred embodiments the resultant alkaline earth metal salt is less soluble and thus forms a precipitate.

The present invention further provides the use of a salt of the first aspect in any manner in which the acidic chelating agent as the free acid or an alkali metal salt thereof is typically used.

As detailed above, the salt of the first aspect is particularly useful in bleaching applications.

The present invention further provides the use of the salt of the first aspect as a chelating agent. In particular the salts of the first aspect of the present invention are used as chelating agents for binding heavy metals and transition metals, for example copper, iron and manganese.

Thus the present invention includes the use of a salt of the first aspect in detergent compositions, for example laundry or automatic dishwashing compositions.

The present invention includes the use of a salt of the first aspect in agricultural applications. For example the salt may be used in slug pellets, in herbicides, in foliar feeds, in nutrient feeds and in hydroponics.

The present invention provides the use of a salt of the first aspect in pulp and paper bleaching. This includes mechanical bleaching and chemical bleaching as well as thermo-mechanical bleaching. The salt of the first aspect may be used in the Q stage and the P stage of the pulp bleaching, that is the wash in which metals are removed and the peroxide stage in which bleaching occurs. These terms are well understood to those skilled in the art.

The present invention provides the use of a salt of the first aspect in personal care applications. For example the salt may be incorporated in hair care compositions, for example hair dyes and shampoo. It may also be included as an antioxidant in creams, for example sun creams and the like. It may be included in dental compositions, for example toothpaste or mouthwashes.

The present invention includes the use of a salt of the first aspect as a biocide potentiator. As such it may be able to increase the effectiveness of a biocide and may find wide application. For example it may be used in personal care applications.

The present invention provides the use of a salt of the first aspect in household, institutional and industrial cleaning applications. It may be included in hard surface cleaners, bathroom and kitchen cleaners, in bottle washing applications or in the cleaning of dairy equipment.

The present invention further provides the use of a salt of the first aspect as an anti-scalant material, for example as a sequestrant of calcium and magnesium salts.

The salt of the present invention may be used in oil field applications as a scale remover, for example to remove barium and strontium salts.

The present invention may provide the use of a salt of the first aspect in metal cleaning applications, for example printed circuit boards or electroless plating applications.

The present invention may provide the use of a salt of the first aspect in medical applications, for example, as an anti-poison material. The present invention may be used to assist the delivery of metals to parts of the body.

Where it is reasonable to do so, any feature of any aspect of the present invention may be combined with any feature of any other aspect. In particular, use of the salt of the first aspect may, where appropriate, include use of a composition of the second aspect.

The present invention provides an alkaline earth metal salt of a chelating agent having an amine functionality which improves the stability of a peroxide bleaching agent, suitably to a greater extent than would be achieved using an equivalent amount of the same chelating agent as the free acid or an alkali metal (e.g. sodium) salt thereof. The present invention therefore allows an improved bleaching performance to be achieved using the same amount of chelating agent; or it allows a lower amount of chelating agent to be used to achieve an equivalent bleaching effect; or it allows a lower amount of peroxygen species to be used to achieve an equivalent bleaching effect.

Thus the present invention further provides the use of a salt of the first aspect to achieve an equivalent bleaching effect in a composition comprising a lower amount of peroxygen species than would be necessary if an equivalent amount of free acid or sodium salt were used.

The present invention also provides the use of a lower amount of a salt of the first aspect to achieve an equivalent bleaching effect compared to the use of the same chelating agent as a sodium salt or free acid in a composition comprising a peroxygen species.

The invention will now be further described by way of the following non-limiting examples.

EXAMPLE 1

Synthesis of MgHEIDA 20 g (0.11 moles) of 2-hydroxyethyliminodiacetic acid, (HEIDA) was slurried in 200 ml of de-ionised water. To this 13.05 g (0.22 moles) $Mg(OH)_2$ was added and the mixture stirred for 17 hours. The solution was concentrated until a white crystalline solid precipitated from the solution. This was collected by filtration and dried in an oven at 40° C. for 24 hours, to provide a compound of formula MgHEIDA.

EXAMPLE 2

Synthesis of CaHEIDA 50 g 2-hydroxyethyliminodiacetic acid, disodium salt (28% active, 0.06 moles) was taken and mixed with 13.9 g (0.12 moles) $CaCl_2$ dissolved in 50 ml deionised water. A white precipitate formed immediately and was collected by filtration. The solid was dried in an oven at 40° C. for 24 hours, to provide a compound of formula CaHEIDA.

EXAMPLE 3

Synthesis of $Mg_2IDS$ 20 g (0.08 moles) of imino disuccinic acid (IDS) was slurried in 200 ml of de-ionised water. To this 9.56 g (0.16 moles) $Mg(OH)_2$ was added and the mixture stirred for 17 hours. The solution was concentration until a white crystalline solid precipitated from the solution. This was collected by filtration and dried in oven at 40° C. for 24 hours, to provide a compound of formula $Mg_2IDS$.

EXAMPLE 4

Synthesis of $Ca_2IDS$ 100 g tetrasodium iminodisuccinate (38% active, 0.1 moles) was taken and mixed with 22.1 g (0.2 moles) $CaCl_2$ dissolved in 50 ml de-ionised water. A white precipitate formed immediately and was collected by filtration. The solid was dried in an oven at 40° C. for 24 hours, to provide a compound of formula $Ca_2IDS$.

EXAMPLE 5

Each of the salts formed in examples 1 to 4 were tested as follows:

125 g of de-ionised water and 25 g of hydrogen peroxide (30% active) were heated to 40° C. 0.1 mmoles of the salt of the chelating agent was added to the solution and the pH was adjusted to 10. The hydrogen peroxide was then monitored over time by periodic titration with potassium permanganate. The results are summarised in tables 1 and 2.

TABLE 1

| Time (min) | $Na_2HEIDA$ (% wt $H_2O_2$ remaining) | MgHEIDA (% wt $H_2O_2$ remaining) | Ca HEIDA (% wt $H_2O_2$ remaining) |
|---|---|---|---|
| 0 | 100 | 100 | 100 |
| 10 | 98 | 98 | 98 |
| 20 | 90 | 96 | 96 |
| 30 | 84 | 93 | 93 |
| 45 | 78 | 86 | 87 |
| 60 | 68 | 80 | 82 |

TABLE 2

| Time (min) | $Na_4IDS$ (% wt $H_2O_2$ remaining) | $Mg_2IDS$ (% wt $H_2O_2$ remaining) | $Ca_2IDS$ (% wt $H_2O_2$ remaining) |
|---|---|---|---|
| 0 | 100 | 100 | 100 |
| 10 | 97 | 97 | 98 |
| 20 | 95 | 95 | 92 |
| 30 | 93 | 97 | 92 |
| 45 | 85 | 95 | 90 |
| 60 | 71 | 95 | 87 |

The invention claimed is:

1. A method of bleaching comprising:
   providing a bleaching composition comprising a peroxygen species;
   improving the stability of the bleaching composition by adding to the bleaching composition a salt comprising an acidic chelating agent comprising an amine functionality and at least 0.25 mole of an alkaline earth metal per mole of acidic protons provided by the chelating agent, wherein the acidic chelating agent is selected from the groups consisting of iminodisuccinic acid and hydroxyethyliminodiacetic acid; and
   contacting the bleaching composition with an object to be bleached;
   wherein the equivalent bleaching effect is achieved using a lower amount of peroxygen species than would be necessary if adding an equivalent amount of free acid or sodium salt of the chelating agent.

2. The method of claim 1, wherein the amount of peroxygen species in said bleaching composition is less than would be necessary in a bleaching composition comprising said free acid or sodium salt.

3. The method of claim 1, wherein the amount of chelating agent in said bleaching composition is less than would be necessary in a bleaching composition comprising said free acid or sodium salt.

4. The method of claim 1, wherein the amount of salt in said bleaching composition is less than would be necessary in a bleaching composition comprising said free acid or sodium salt.

5. The method of claim 1, wherein the acidic chelating agent is iminodisuccinic acid.

6. The method of claim 1, wherein the acidic chelating agent is hydroxyethyliminodiacetic acid.

7. The method of claim 1, Wherein the alkaline earth metal is selected from the group consisting of calcium, magnesium and mixtures thereof.

8. The method of claim 1, wherein the peroxygen species is selected from the group consisting of hydrogen peroxide, perborate and percarbonate.

9. The method of claim 1, wherein the salt is selected from the group consisting of dicalcium iminodisuccinic acid ($Ca_2IDS$), calcium magnesium iminodisuccinic acid (CaMgIDS), dimagnesium iminodisuccinic acid ($Mg_2IDS$), dicalcium hydroxyethyliminodiacetic acid ($Ca_2HEIDA$), calcium magnesium hydroxyethyliminodiacetic acid (CaMg-HEIDA) and dimagnesium hydroxyethyliminodiacetic acid ($Mg_2HEIDA$) and non-stoichiometric equivalents thereof.

10. The method of claim 1, comprising at least 0.4 mole of an alkaline earth metal per mole of acid protons provided by the chelating agent.

* * * * *

UNITED STATES PATENT AND TRADEMARK OFFICE
CERTIFICATE OF CORRECTION

| | |
|---|---|
| PATENT NO. | : 8,801,962 B2 |
| APPLICATION NO. | : 13/146322 |
| DATED | : August 12, 2014 |
| INVENTOR(S) | : Matthew Robert Giles et al. |

It is certified that error appears in the above-identified patent and that said Letters Patent is hereby corrected as shown below:

In the Claims

Column 12, line 9 (claim 7), "Wherein" should read -- wherein --

Column 12, line 14 (claim 8), "perhorate and percarhonate" should read -- perborate and percarbonate --

Signed and Sealed this
Twenty-first Day of October, 2014

Michelle K. Lee
*Deputy Director of the United States Patent and Trademark Office*